United States Patent [19]

Addor et al.

[11] Patent Number: 5,030,735

[45] Date of Patent: Jul. 9, 1991

[54] PROCESS FOR THE PREPARATION OF INSECTICIDAL, ACARICIDAL AND NEMATICIDAL 2-ARYL-5-(TRIFLUOROMETHYL) PYRROLE COMPOUNDS

[75] Inventors: Roger W. Addor, Pennington; Joseph A. Furch, Lawrenceville, both of N.J.; David G. Kuhn, Newtown, Pa.

[73] Assignee: American Cyanamid Company, Stamford, Conn.

[21] Appl. No.: 560,396

[22] Filed: Jul. 31, 1990

[51] Int. Cl.$^5$ ............... C07D 207/333; C07D 207/335; C07D 207/337

[52] U.S. Cl. .................................. 548/531; 548/557; 548/560; 548/561

[58] Field of Search ................ 548/531, 557, 560, 561

[56] References Cited

PUBLICATIONS

S. M. Albonico et al., Journal of Organic Chemistry, 43, pp. 4273–4276, (1978).

Brown, et al., vol. 111 (1989), 111:194576w.

*Primary Examiner*—Joseph Paul Brust
*Attorney, Agent, or Firm*—John W. Hogan, Jr.

[57] ABSTRACT

There is provided a process for the preparation of 2-aryl-5-(trifluoromethyl)pyrrole compounds which are useful as insecticidal, acaricidal and nematicidal agents.

5 Claims, No Drawings

PROCESS FOR THE PREPARATION OF INSECTICIDAL, ACARICIDAL AND NEMATICIDAL 2-ARYL-5-(TRIFLUOROMETHYL) PYRROLE COMPOUNDS

BACKGROUND OF THE INVENTION

Arylpyrrole compounds useful as insecticides, nematicides and acaricides and the preparation thereof by the reaction of an azalactone with an α-halo-α,β-unsaturated nitrile, ester or nitro compound in the presence of a nonpolar solvent are described in copending patent application Ser. No. 392,495, filed on Aug. 11, 1989, no abandoned. The process of said copending application is useful for the preparation of said arylpyrroles. However, the reaction produces only moderate product yields, uses large excesses of the α-halo-α, β-unsaturated nitrile, ester or nitro compound and requires long reaction times.

It is an object of the present invention to provide a more efficient process for the preparation of insecticidal, nematicidal and acaricidal 2-aryl-5-(trifluoromethyl)pyrrole compounds which reduces excess starting materials and reaction time and increases product yield.

SUMMARY OF THE INVENTION

The present invention relates to a process for the preparation of insecticidal, nematicidal and acaricidal 2-aryl-5-(trifluoromethyl)pyrrole compounds of formula I

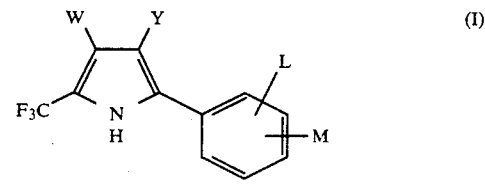

wherein
W is $C_1$–$C_4$ alkyl, $CF_3$ or H;
Y is CN, $NO_2$ or $CO_2R$;
R is $C_1$–$C_4$ alkyl;
L is H, F, Cl or Br;
M is H, F, Cl, Br, I, $CF_3$, $NO_2$ or $OR_1$; and
$R_1$ is $C_1$–$C_3$ alkyl or $C_2F_4H$ by a single step reaction between an azalactone compound of formula II (II)

wherein L and M are as described above and an α-halo-α,β-unsaturated nitrile, ester or nitro compound of formula III (III)

wherein W and Y are as described above; X is Cl, Br, I or

and the cis and trans isomers thereof in the presence of a polar solvent and a base.

DETAILED DESCRIPTION OF THE INVENTION

The present invention provides a process for the preparation in good yield of insecticidal, nematicidal and acaricidal compounds of formula I (I)

wherein
W is $C_1$–$C_4$ alkyl, $CF_3$ or H;
Y is CN, $NO_2$ or $CO_2R$;
R is $C_1$–$C_4$ alkyl;
L is H, F, Cl or Br;
M is H, F, Cl, Br, I, $CF_3$, $NO_2$ or $OR_1$; and
$R_1$ is $C_1$–$C_3$ alkyl or C by an efficient single step reaction between an azalactone compound of formula II (II)

wherein L and M are as described above and an α-halo-α, β-unsaturated nitrile, ester or nitro compound of formula III (III)

wherein W and Y are as described above; X is Cl, Br, I or $$\overset{O}{\underset{\|}{O\overset{}{C}CH_3}}$$

and the cis and trans isomers thereof in the presence of a polar solvent and a base.

The process preferably comprises reacting a formula II azalactone as described above with at least about one molar equivalent, preferably about one to five molar equivalents, of a formula III α-halo-α,β-unsaturated nitrile, ester or nitro compound as described above and at least about one molar equivalent, preferably about one to five molar equivalents, of a base in the presence of a polar solvent preferably at a temperature range of about 20° C. to 180° C. to form 2-aryl-5-(trifluoromethyl)pyrrole compounds of formula I. Naturally, it is especially preferred to use as little excess reactants as possible. Advantageously, stoichiometric quantities may be used in the present invention and still maintain good yields.

The product formula I compounds may be isolated by conventional techniques such as dilution of the reaction mixture with water and filtration of the formula I product or extraction of said product with a suitable solvent. In the isolation procedure any suitable extraction solvents may be employed, including water-immiscible solvents such as ether, ethyl acetate, methylene chloride and the like.

Bases suitable for use in the process of the invention include bases such as alkali metal carbonates, $C_1$–$C_4$ trialkylamines, alkali metal hydroxides and pyridine. Preferred bases are pyridine, triethylamine and sodium carbonate.

Reaction solvents suitable for use in the above process include any polar solvents, for example solvents such as acetonitrile, dimethylsulfoxide, dimethylformamide, ethanol, methanol and isopropanol. Acetonitrile and dimethylformamide are preferred reaction solvents.

Certain starting formula III compounds are described in copending patent application Ser. No. 07/560,403 filed concurrently herewith and incorporated herein by reference thereto. Formula II azalactone compounds used in the present invention are described in copending patent application Ser. No. 329,495, filed on Aug. 11, 1989, now abandoned and which is incorporated herein by reference thereto.

In order to facilitate a further understanding of the invention, the following examples are presented to illustrate more specific details thereof. The invention is not to be limited thereby except as defined in the claims.

EXAMPLE I

Preparation of 2-Phenyl-5-(trifluoromethyl)pyrrole-3-carbonitrile in the presence of a base.

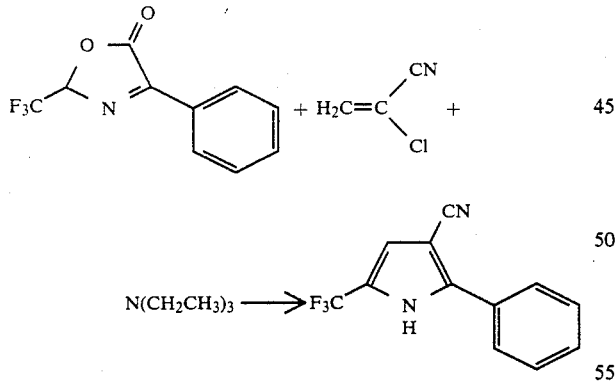

Triethylamine (4.5 g, 0.044 mol) is added dropwise to a mixture of 4-phenyl-2-(trifluoromethyl)-5(2H)-oxazolone (10.0 g, 0.043 mol), 2-chloroacrylonitrile (3.51 g, 0.43 mol) and acetonitrile (50 mL). The temperature of the reaction mixture rises to 65° C. and carbon dioxide gas evolves during the addition. After the addition is complete the reaction mixture is heated at reflux temperature for one hour, cooled to room temperature and poured into water (150 mL). The solids are collected by filtration, air-dried and dried under vacuum at 60° C. to give the title compound as a white solid (10.05 g, 97%). Identified by NMR spectral analyses.

The process described affords a nearly quantitative yield of the product pyrrole using stoichiometric amounts of reagents and short reaction time.

EXAMPLE 2

Preparation of 2-Phenyl-5-(trifluoromethyl)pyrrole-3-carbonitrile without added base

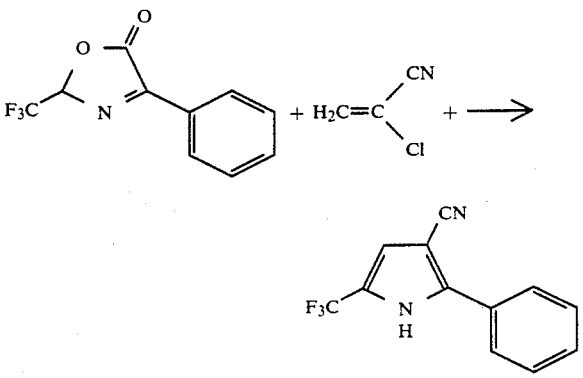

4-Phenyl-2-(trifluoromethyl)-5(2H)-oxazolone (13.5 g, 0.059 mol), 2-chloroacrylonitrile (26 mL, 0.295 mol) and acetonitrile (250 mL) are heated at reflux temperature for 52 hours. The reaction mixture is then cooled to room temperature and concentrated in vacuo to give a solid. Recrystallization of the solid from toluene gives the title product as a yellow solid 10.1 g, 73%). Identified by NMR spectral analyses.

The procedure without added base gives only a yield of the title product despite the use of a large excess of 2-chloroacrylonitrile and a long reaction time.

EXAMPLE 3

Preparation of Methyl 2-(p-chlorophenyl)-5-(trifluoro-methyl)pyrrole-3-carboxylate

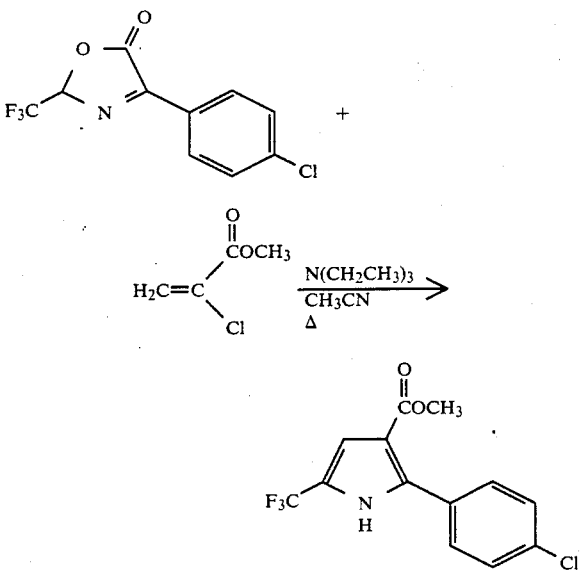

Triethylamine (5.58 g, 0.055 mol) is added dropwise to a mixture of 4-(p-chlorophenyl)-2-(tri-fluoromethyl)-5(2H)-oxazolone (15.6 g, 0.054 mol), methyl α-chloroacrylate (6.52. g, 0.054 mol) and acetonitrile (50 mL).

The reaction mixture heats up to 55° C. during the addition. After the addition is complete, the reaction mixture is heated at reflux temperature for one hour, cooled to room temperature and filtered. The filtrate is poured into an ether/water mixture and extracted with ether. The combined organic extracts are dried over anhydrous magnesium sulfate and concentrated in vacuo to give a black residue. Recrystallization of the residue from hexane gives the title compound as an orange solid (8.25 g, 50.2%). Indentified by NMR spectral analyses.

EXAMPLE 4

Preparation Using Non-Polar Solvent Instead of Polar Solvent

This example shows the necessity of using a polar solvent. Surprisingly, the base-catalyzed reaction when run in the presence of a non-polar solvent such as toluene does not result in the desired pyrrole.

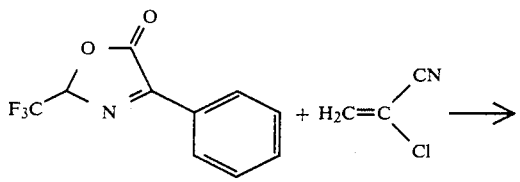

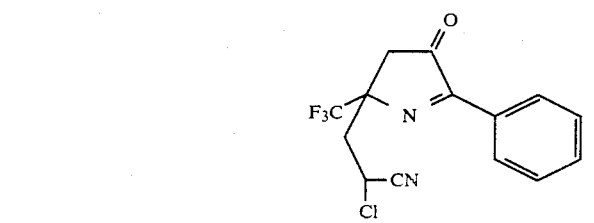

2-chloroacrylonitrile (3.85 g, 0.044 mol) is added to a 0° C. mixture of 4-phenyl-2-(trifluoromethyl)(5(2H)-oxazolone (10.0 g, 0.044 mol) and toluene (50 mL). Triethylamine (4.49 g, 0.044 mol) is added dropwise to the reaction mixture and the temperature rises to 25° C. When the addition is complete, water is added to the reaction mixture and the layers are separated. The organic layer is dried over anhydrous magnesium sulfate and concentrated in vacuo to give alpha-chloro-5-oxo-4-phenyl-2 -(trifluoromethyl)-3-oxazoline-2-propionitrile as an amber liquid (8.37 g, 60%). Identified by NMR spectral analyses.

EXAMPLE 5

This example demonstrates that with the addition of a base and a polar solvent such as acetonitrile to the product formed in Example 4 the desired pyrrol is formed.

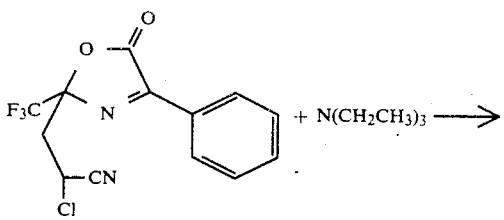

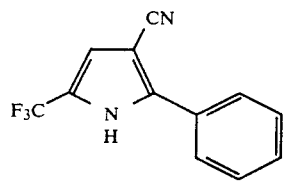

Triethylamine (0.077 g, 0.76 mmol) is added dropwise to a refluxing mixture of alpha-chloro-5-oxo-4-phenyl-2-(trifluoromethyl)-3-oxazoline-2-propionitrile (0.24 g, 0.76 mmol) and acetonitrile (25 mL). The reaction mixture is refluxed for 2 hours, cooled to room temperature and poured into water. The solids are collected by filtration and dried to give the title compound as a white solid (0.16 g, 88%). Identified by NMR spectral analyses.

EXAMPLE 6

Solvent and base effects upon 2-aryl-5-(trifluoromethyl)pyrrole formation

The effects of solvents and base changes on the synthesis of 2-phenyl-5-(trifluoromethyl)pyrrole-3-carbonitrile from 4-phenyl-2-(Trifluoromethyl)-5-(2H)-oxazolone and 2-chloroacrylonitrile are shown in Table I. The percentages shown represent area percent determined by HPLC analysis of the reaction mixture after refluxing for 178 hour.

TABLE I

| Solvent and Base Effects | | |
|---|---|---|
| Solvent | Base | % Yield Arylpyrrole |
| Toluene | Triethylamine | 11 |
| Toluene | Pyridine | 8 |
| Tetrahydrofuran | Triethylamine | 39 |
| Ethanol | Triethylamine | 80 |
| Acetonitrile | Triethylamine | 96 |
| Acetonitrile | — | 4* |
| Dimethylformamide | Pyridine | 100 |
| Dimethylformamide | Sodium carbonate | 74 |
| Dimethylformamide | Triethylamine | 100 |

*1 hour refluxing

EXAMPLE 7

Base effects in 2-aryl-5-(trifluoromethyl)pyrrole formation

Base effects on the synthesis of 2-aryl-5-(trifluoromethyl)pyrroles are shown in Table II. Acetonitrile is the solvent in all reactions.

TABLE II

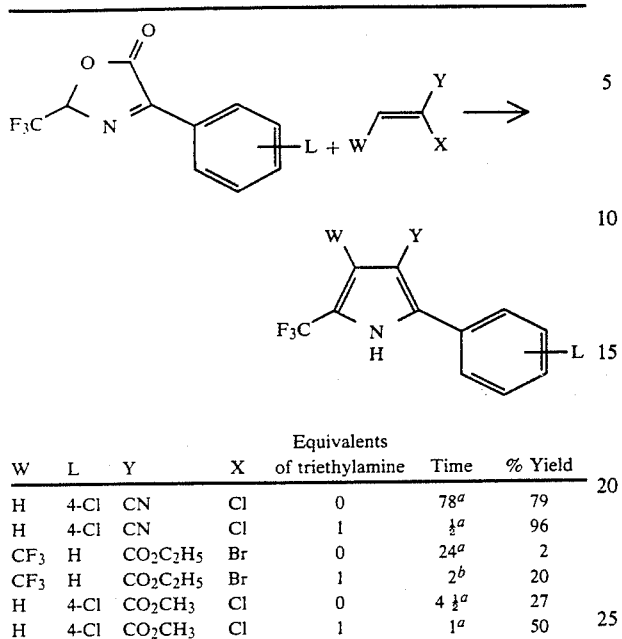

| W   | L    | Y         | X  | Equivalents of triethylamine | Time    | % Yield |
|-----|------|-----------|-----|------------------------------|---------|---------|
| H   | 4-Cl | CN        | Cl  | 0                            | 78$^a$  | 79      |
| H   | 4-Cl | CN        | Cl  | 1                            | ½$^a$   | 96      |
| CF₃ | H    | CO₂C₂H₅   | Br  | 0                            | 24$^a$  | 2       |
| CF₃ | H    | CO₂C₂H₅   | Br  | 1                            | 2$^b$   | 20      |
| H   | 4-Cl | CO₂CH₃    | Cl  | 0                            | 4½$^a$  | 27      |
| H   | 4-Cl | CO₂CH₃    | Cl  | 1                            | 1$^a$   | 50      |

$^a$Hours reaction mixture is refluxed.
$^b$Hours reaction mixture is stirred at room temperature.

EXAMPLE 8

Solvent effects in 2-aryl-5-(trifluoromethyl)pyrrole formation

Solvent effects in the formation of 2-(p-chlorophenyl-5-(trifluoromethyl)pyrrole-3-carbonitrile from 4-(p-chlorophenyl)-2-(trifluoromethyl)-5(2H)-oxazolone and 2-chloroacrylonitrile are shown in Table III.

TABLE III

Solvent effects in 2-aryl-5-(trifluoromethyl)pyrrole formation

| Solvent                 | Equivalents of 2-Chloroacrylonitrile | Time$^a$ | % Yield |
|-------------------------|--------------------------------------|----------|---------|
| Nitromethane            | 10                                   | 21       | 14      |
| Toluene                 | 10                                   | 17       | 17      |
| Trifluoroacetic Anhydride | 10                                 | 17       | 17      |
| Acetonitrile            | 10                                   | 17       | 46      |

$^a$Hours reaction mixture is refluxed

The results of these experiments show that even with polar solvents and long times, yields are generally poor in the absence of added base.

What is claimed is:

1. A process for the preparation of a first compound having the structural formula:

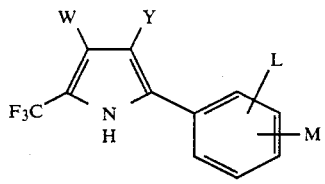

wherein
W is $C_1$–$C_4$ alkyl, $CF_3$ or H;
Y is CN, $NO_2$ or $CO_2R$;
R is $C_1$–$C_4$ alkyl;
L is H, F, Cl or Br;
M is H, F, Cl, Br, I, $CF_3$, $NO_2$ or $OR_1$; and
$R^1$ is $C_1$–$C_3$ alkyl or $C_2F_4H$ which comprises reacting a second compound having the structure

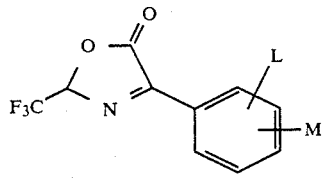

wherein L and M are as described above with at least about 1 molar equivalent of a third compound having the structure $$\underset{W}{\overset{H}{\diagdown}}C=C\underset{X}{\overset{Y}{\diagup}}$$

wherein W and Y are as described above, X is Cl, Br, I or $$\underset{\parallel}{\overset{O}{\underset{}{\text{OCCH}_3}}}$$

and the cis and trans isomers thereof in the presence of at least about 1 molar equivalent of a base and a polar solvent to form said first compound.

2. The process according to claim 1 wherein the base is an alkali metal carbonate, $C_1$–$C_4$ trialkylamine or pyridine, and the polar solvent is acetonitrile, dimethylformamide, dimethylsulfoxide, ethanol, methanol or isopropanol.

3. The process according to claim 2 wherein the base is triethylamine.

4. The process according to claim 2 wherein the polar solvent is acetonitrile.

5. The process according to claim 2 wherein the temperature of the reaction mixture is about 20° to 180° C.

* * * * *

UNITED STATES PATENT OFFICE
CERTIFICATE OF CORRECTION

Patent No. 5,030,735      Dated July 9, 1991

Inventor(s) Roger Williams Addor et al.

It is certified that error appears in the above-identified patent and that said Letters Patent is hereby corrected as shown below:

Claim 1, Column 8, lines 10 to 11 wherein
  W is $C_1$-$C_4$ alkyl CF3, or H;

should read wherein
  W is $C_1$-$C_4$ alkyl, $CF_3$ or H;

Signed and Sealed this

Twenty-third Day of February, 1993

Attest:

STEPHEN G. KUNIN

*Attesting Officer*      *Acting Commissioner of Patents and Trademarks*